United States Patent [19]

Swank et al.

[11] Patent Number: 4,810,657

[45] Date of Patent: Mar. 7, 1989

[54] METHOD OF DIAGNOSING MULTIPLE SCLEROSIS AND OTHER DISEASES BY MEASUREMENT OF BLOOD PLASMA PROTEIN STREAMING POTENTIAL

[76] Inventors: Roy L. Swank, 2211 SW. 1st Ave., Portland, Oreg. 97201; James W. Goodwin, Chatleigh House, 6 Warminster Road, Limpley Stoke, Bath, BA36JD, England

[21] Appl. No.: 109,941

[22] Filed: Oct. 19, 1987

[51] Int. Cl.$^4$ .................... A61K 39/00; G01N 25/08; G01N 1/00; A61B 5/00
[52] U.S. Cl. .................................. 436/150; 436/149; 436/151; 436/174; 424/88; 128/734; 128/637
[58] Field of Search ............... 436/150, 149, 151, 174; 128/637, 668, 434, 905

[56] References Cited

U.S. PATENT DOCUMENTS

| | | | |
|---|---|---|---|
| 4,294,818 | 10/1981 | McMichael et al. | 424/88 |
| 4,311,686 | 1/1982 | Angers et al. | 435/3 |
| 4,425,922 | 1/1984 | Conti et al. | 128/691 |
| 4,705,756 | 11/1987 | Spillert et al. | 436/64 |

Primary Examiner—Benoit Castel
Assistant Examiner—Lyle Alfandary Alexander
Attorney, Agent, or Firm—Eugene D. Farley

[57] ABSTRACT

Multiple sclerosis and other diseases are diagnosed by first coating a plasm protein-adsorbing surface with a patient's blood plasm protein in an electrolyte fluid, and measuring the streaming potential of the protein-coated surface. Next, a challenge material such as a fatty acid having from 6 to 24 carbon atoms is added to the protein in electrolyte fluid mixture to alter the electrokinetic potential of the adsorbed blood plasm protein layer. The streaming potential of the altered layer then is measured. The streaming potential results thus obtained are compared with measurements of the streaming potential characteristic of a surface similarly treated, but using normal blood plasma protein.

16 Claims, 1 Drawing Sheet

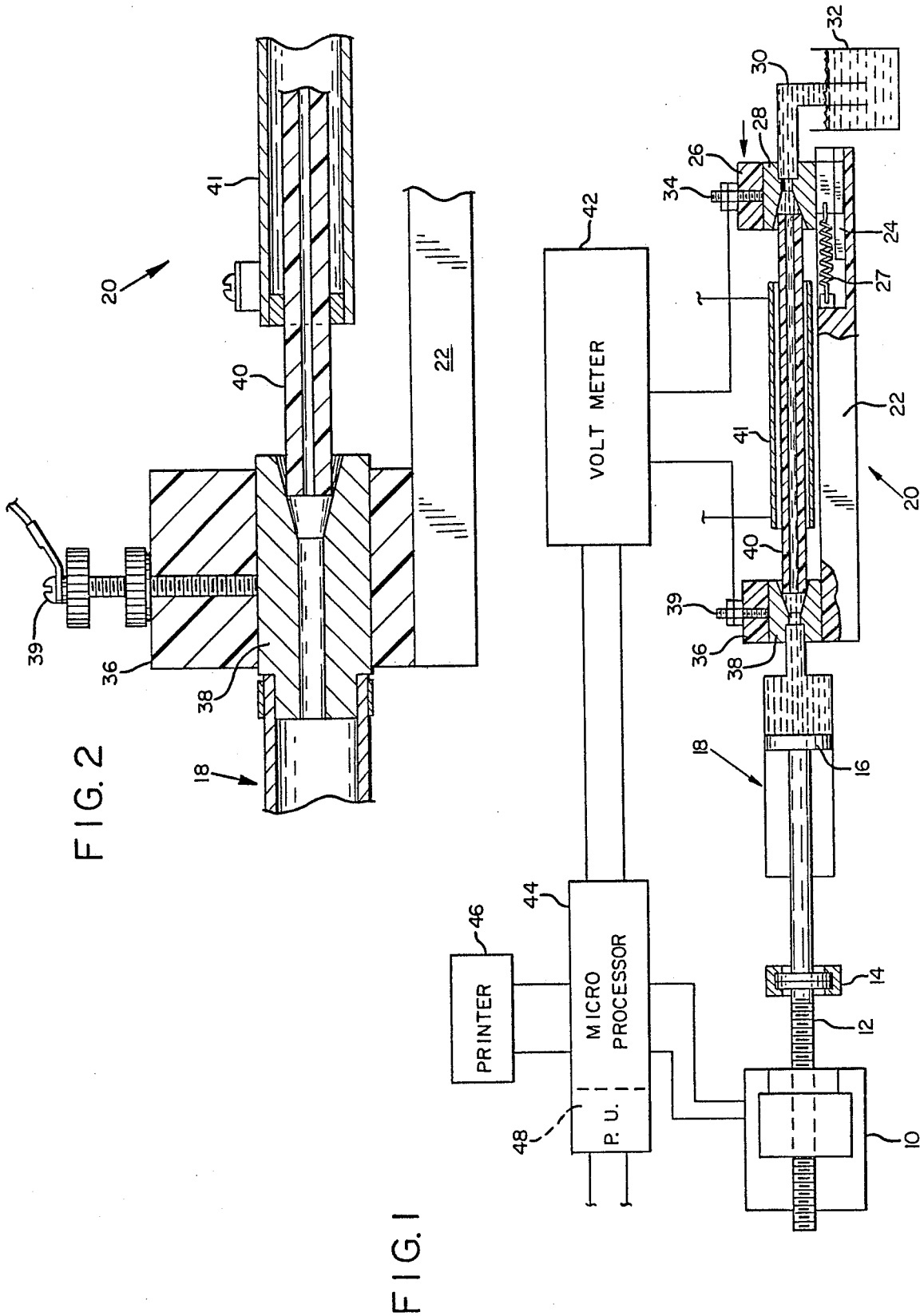

METHOD OF DIAGNOSING MULTIPLE SCLEROSIS AND OTHER DISEASES BY MEASUREMENT OF BLOOD PLASMA PROTEIN STREAMING POTENTIAL

BACKGROUND OF THE INVENTION

This invention relates to a method of diagnosing diseases by noting the streaming potential characteristics of a surface coated with the blood plasma protein of the patient.

The phenomenon of streaming potential is observed when a charged surface is placed in contact with water or an electrolyte solution such as a salt solution. In such a situation, there is a diffuse layer of ions held close to the surface which exactly balances the charge of the charged surface. If the fluid is caused to flow parallel to the charged surface, a charge separation is produced which gives rise to an electric potential difference. This is known as streaming potential.

It is to be noted, however, that there is a diffuse distribution of the attracted ions close to the charged surface, with the result that the electric potential falls off with increasing distance from the surface. When the fluid is caused to move across the surface, resulting in the creation of a streaming potential, the ions comprising the surface layer are stuck to the charged surface and don't move. The first ion movement is just outside this layer at a position known as the shear plane.

The potential of the shear plane may be calculated from the measurement of streaming potential and is known as the zeta potential.

Zeta potential values are determined by mathematical computation from streaming potential values and accordingly are derivative values. They are useful because they are independent of stream flow rates. In the present discussion the two terms "streaming potential" and "zeta potential" are used interchangeably, since they represent two different modes of expression of the characteristic which is useful in the diagnosis of disease by the presently described method.

SUMMARY OF THE INVENTION

We have discovered that in the blood plasma proteins of victims of certain diseases, particularly multiple sclerosis, there are abnormalities present which affect the streaming potential characteristics of surfaces on which they are adsorbed. This fact may be used as a basis for the diagnosis of the disease. In other words, the presence or absence of variations of streaming potential values gives an indication of whether or not the plasma has been obtained from a person suffering from the disease.

The method consists simply of coating a suitable surface with normal blood plasma protein and thereafter applying to the surface a material, termed herein a "challenge" material, which also is capable of being adsorbed on the surface. In effect, it competes with the blood plasma protein in this regard, with the result that a new coated surface is formed in which the new coating is formed partly of normal blood plasma protein and partly of the challenge material molecules, or of a reaction product of the protein and the challenge material. This surface has different streaming potential characteristics than has the original surface.

The basis for the present discovery lies in the fact that the challenge material reacts differently toward the blood plasma protein of a diseased person than it does toward the blood plasma protein of a normal person. This difference is reflected in a difference in streaming potential (zeta potential) values.

Accordingly, by comparing the streaming potential values obtained for a surface coated with challenged diseased blood plasma proteins with the values obtained for the same surface coated with challenged normal blood plasma proteins, a method is made available for diagnosing whether a given plasma is that of a normal or diseased person. The method may be extended also to veterinary use by substituting the blood plasma of animals suspected of having a given disease, for the blood of human patients.

BRIEF DESCRIPTION OF THE DRAWINGS

In the drawings:

FIG. 1 of the drawings illustrates schematically apparatus which may be used for measuring the streaming potential values of blood plasma protein-coated surfaces useful in obtaining streaming potential values indicative of the presence or absence of a given disease, thereby affording a method of diagnosis.

FIG. 2 is an enlarged view of a portion of the apparatus of FIG. 1.

DESCRIPTION OF THE PREFERRED EMBODIMENTS

As noted above, the herein described method of disease diagnosis using streaming potential values as a diagnostic aid comprises the following basic steps:

First, a suitable surface is coated with normal blood plasma protein, forming a normal protein-coated surface.

Second, an electrolyte is passed across the protein-coated surface at a predetermined and substantially uniform rate and the streaming potential (zeta potential) developed is measured.

Third, a challenge material is applied to the normal protein-coated surface, forming an altered protein-coated surface.

Fourth, an electrolyte solution is passed across the altered protein-coated surface at a predetermined and substantially uniform rate, and the streaming potential (zeta potential) developed is measured.

Next the above steps are repeated, using patient blood plasma suspected of being diseased blood plasma. If this indeed is the case, a different change in streaming potential value will be obtained, thereby providing a method of diagnosing the disease.

It will be apparent that in order to carry out the foregoing sequence there are required:

1. A suitable plasma protein-adsorbing surface.
2. Samples of normal and patient blood plasma.
3. An effective challenge material and,
4. A suitable electrolyte solution.

Considering these components in turn:

A variety of materials provide surfaces suitable for use in determining streaming potential, and accordingly are suitable for use in the present invention. The primary characteristic reqired is that of having the capacity of adsorbing strongly blood plasma protein molecules. The surface accordingly should be hydrophobic.

Represetative of materials providing suitable hydrophobic surfaces are Polystyrene, Polyethylene, Nylon, and Lucite. Glass coated with silanes or other materials to render it hydrophobic also may be used. Of this group, Polystyrene in the form of a disposable capillary tube is preferred.

With respect to the blood plasma component, it is noted that as compared with other blood products such as whole blood and blood serum, blood plasma is unique in its suitability for use in the presently described method. We have found that whole blood is not suitable for use in our method since it contains too high a salt concentration to obtain valid streaming potential readings. If diluted to suitable concentration levels, the resulting osmotic pressure causes the cell membranes to rupture, giving rise during streaming potential determination to problems such as electrode fouling.

Blood serum is not suitable, since it comprises merely the watery portion of the blood remaining after protein coagulation and removal. It does not contain the proteins which are required for surface adsorption and streaming potential determination in the presently described method.

Blood plasma, on the other hand, comprises the fluid part of the blood, including water, albumin, fibrin, and various salts. It is obtained by adding sodium citrate or other anti-coagulant to the blood, after which the blood is centrifuged for separation of the cellular components, including the red and white cells, which are removed. The resulting blood plasma product is similar to that comprising Red Cross blood bank blood.

The plasma is used in amount sufficient to coat the adsorbing surface relatively completely.

The third component of our diagnostic system comprises the "challenge" material. By this is meant a material which alters the electro-kinetic potential of the adsorbed blood plasma protein layer so that the streaming potential properties thereof are affected. The material desorbs, or reacts with, the protein in a manner not presently known. In any event, the reaction of the challenge material with normal blood protein and with diseased blood protein is different, so that different streaming potential values are obtained. This in turn offers a means of diagnosis of a diseased condition.

Preferred challenge materials for use in the present invention comprise the higher fatty acids having from 6 to 24 carbon atoms, preferably from 16 to 22 carbon atoms. Illustrative members of this group comprise linoleic acid, oleic acid, caprylic acid, undecenoic acid, and fumaric acid.

Although the exact mechanism is not known, these materials appear to have the property of not attacking normal plasma protein adsorbed on the surface. However, they do attack, or shear off from the surface, some of the diseased plasma protein, for example that derived from a patient suffering from multiple sclerosis, so that different streaming potential values are obtained.

In practicing the invention, sufficient of the challenge material is used to give a significant, preferably the maximum, alteration in streaming potential values without unduly contaminating the fluid medium with an excess of challenge material. This may be accomplished, for example, by adding increasing amounts of challenge material to the fluid medium and observing the corresponding changes in streaming potential values. When maximum change has been achieved, the optimum amount of challenge material has been added.

The fourth component of the herein described diagnostic system is the eletrolytic fluid passed across the protein-coated surface in the determination of streaming potential.

Various electrolyte solutions may be employed, provided they do not react with the electrodes of the streaming potential apparatus, or with the blood plasma protein, or with the challenge material. For example, potassium salts are unsuitable for use in the electrolyte when silver electrodes are employed, since they attack the electrodes.

For reasons of availability, effective action, and failure to react deleteriously with either the system electrodes or the protein coating, aqueous solutions of common salt (sodium chloride) comprise preferred electrolyte solutions. Also, sodium chloride is a constituent of blood plasma, insuring compatibility.

Although sodium chloride is a preferred material, other electrolytes such as magnesium sulphate may be used.

In general the electrolyte is used in an amount sufficient to produce an electrolyte solution having an ionic strength in range of from $10^{-1}$ to $10^{-5}$. Where sodium chloride is employed, saline concentrations of up to 0.01 molar (600 mg/ltr.) are satisfactory.

Where the ionic strengths are too high, loss of sensitivity results and the streaming potential values obtained tend to be too small to be significant. Where the ionic strength values are too low, polarization of the electrodes may occur.

EXAMPLES

The presently described diagnostic method may be carried out in the apparatus illustrated schematically in the drawings.

A variable speed motor 10 drives a reciprocating screw 12 coupled through coupling 14 to the piston 16 of a syringe pump 18. The syringe pumps fluid through the streaming potential measuring unit indicated generally at 20.

The latter unit is mounted on a base 22 formed with a longitudinal guideway 24. A sliding block 26 of Plexiglass or other suitable material, biased in the direction of the arrows by spring 27, is mounted in the guideway. It, in turn, is provided with a transverse channel which mounts a connector 28 communicating with a tube 30 which discharges into reservoir 32. Sliding block 26 also mounts a first electrode 34 in electrical contact with connector 28.

Base 22 also mounts a fixed block 36 having therethrough a transverse opening which receives a connector 38 communicating with the discharge end of syringe 18. It mounts further an electrode 39 which is in electrical contact with connector 38 and cooperates with electrode 34 of block assembly 26.

Connectors 28, 38 mount releasably between them a replaceable cell 40 which, as noted above, may comprise a replaceable capillary tube made of Polystyrene, Polyethylene, Nylon, Lucite, hydrophobic coated glass, or other suitable material.

In operation, motor driven syringe pump 18 reversably circulates fluid through replaceable cell 40. Cell 40 is surrounded by an earthed screen 41 to eliminate the effect of any stray potentials present.

Streaming potential develops between electrodes 34, 39. This is measured in voltmeter 42 electrically connected to microprocessor control unit 44 and associated printer 46, driven by power unit 48. The control unit, in turn, controls variable speed motor 10.

In the operation of the system, a fresh cell 40 is placed in the unit and saline placed in reservoir 32. Motor 10 is started, driving syringe pump 18 in reciprocating motion. This flushes cell 40 with the saline solution.

Normal blood plasma in the predetermined amount then is added to the saline solution in reservoir 32 or, in the alternative, the saline solution is removed and replaced with a solution of the calculated concentration of plasma in saline. An exemplary mixture of electrolyte solution and plasma will contain from about 0.1 to about 0.8 grams of plasma per 200 milliliters of electrolyte solution.

The new charge then is pumped back and forth in the cell and the voltage observed on voltmeter 42. The linoleic acid or other challenge material in the predetermined and calculated amount then is added to the reservoir and the new streaming potential voltage readings observed. In a typical instance, from 4 to 20 milligrams of challenge material are added to 65 milligrams of plasma protein.

The sequence of operations is repeated, but using blood plasma derived from a patient suspected of having multiple sclerosis or other disease.

The readings are compared and, if there is a deviation of more than a certain threshold value, for example 4%, a positive diagnosis is indicated.

During this procedure microprocessor control unit 44 assists by controlling the speed of motor 10, and hence of syringe pump 18; the direction of flow; and the number of cycles of operation. Printer 46 records the pump speed and the number of cycles. It also can be set up to graph the voltage versus the time, thereby facilitating reaching a conclusion as to the stability of the operating conditions. These are pH, temperature, and flow rate.

Although the pH value at which the measurements are made are somewhat variable, for best results the pH should be controlled within the range of from pH 4 to pH 10, preferably within the range of from pH 6 to pH 8. This may be accomplished by the addition of appropriate buffers. For example, where the electrolyte solution comprises a saline solution, a sodium bicarbonate buffer may be employed. The pH remains substantially the same throughout the entire determination.

Since streaming potential values vary with temperature, it is important that the temperature be maintained constant during the run. To this end, it is desirable to place reservoir 32 in a thermostat bath. The temperature of the fluid tested should be maintained within a range of plus or minus 1° C. The temperature may be maintained appropriately at ambient temperatures, or at normal body temperature.

The flow rate should be maintained constant for each series of measurements. However, it is desirable to vary the flow rate from series to series by varying the speed of operation of pump 18. An average thus can be obtained, which is more significant than the results of a single run.

The potential developed varies linearly with the flow rate. Accordingly, before and after the challenge material addition, the flow rate must be the same. The higher the flow rate, the bigger the potential difference. In general, however, (for best results) it is desirable to keep the flow rate at a value which promotes linear flow, as opposed to turbulent flow.

In a specific example, illustrating our invention, a 0.001 molar sodium chloride solution was buffered with a solution of sodium bicarbonate of like concentration to give an electrolyte solution having a pH of 7.0. A 200 cubic centimeter aliquot was placed in reservoir 32 and syringe pump 18 filled. Air bubbles were expelled from both the syringe and associated tubing, including the replaceable capillary test section 40, which was made of polystyrene.

The syringe pump was started and the potential measured with flow in both directions. This was carried out over a range of flow values to insure that a good linear relationship with flow rate was obtained.

An aliquot of plasma (800 milligrams) was added to the reservoir and mixed. After four syringe fill and emptying actions, the system was left to stand for about ten minutes to allow adsorption and coating to become complete. The potential again was determined. It was considerably lower than for the uncoated tube.

Next 3.0 milliliters of a 2.5% linoleic acid solution was added to the reservoir to provide a challenge material. After mixing, the potential again was measured.

The foregoing sequence was repeated, using plasma obtained from a patient suspected of having multiple sclerosis. The two sets of data were compared. In all cases it was found that there was a significant increase of streaming potential values in the case of capillary tubes exposed to plasma from patients having the disease.

In all of the above work, the electrical conductivity was measured and the data used as a basis for calculation of the zeta potential, i.e. the potential at the shear plane adjacent the surface of the adsorbed blood plasma protein coating. The values thus obtained are summarized in the following table, from which the significant effect of substituting diseased plasma for normal plasma on the determination of streaming potential is clearly apparent.

| | | STREAMING POTENTIALS & ZETA-POTENTIALS OF PLASMA COATED TUBE SURFACES | | | | |
|---|---|---|---|---|---|---|
| | | Before Addition of Challenge Material | | After Addition of Challenge Material | | % Change of Zeta Potential |
| | | Streaming Potential (mV) | Zeta Potential (mV) | Streaming Potential (mV) | Zeta Potential (mV) | |
| Control* | 1 | −4.51 | −22.5 | −6.09 | −29.5 | +32 |
| Control | 2 | −6.21 | −29.4 | −8.51 | −35.5 | +33 |
| Control | 3 | | | | | +13 |
| Control | 4 | | | | | −3 |
| | | | | | average | +19 |
| MS** | 1 | −4.16 | −18.3 | −6.90 | −30.6 | +63 |
| MS | 2 | −4.67 | −23.8 | −6.65 | −33.0 | +39 |
| MS | 3 | | | | | +56 |
| MS | 4 | | | | | +17 |
| | | | | | average | +44 |

*Control: normal healthy plasma
**MS: multiple sclerosis - diseased plasma

The above procedure was repeated using various challenge materials other than linoleic acid, with results as follows:

| | AVERAGE % CHANGE OF ZETA POTENTIAL |
|---|---|
| SATISFACTORY | |
| Oleic acid | 20 |
| Undecenoic acid | 13 |
| Fumaric acid | 9 |
| UNSATISFACTORY | |
| Succinic acid | 3 |
| Phenylacetic acid | 3 |
| Cinnamylidenacetic acid | 2 |
| Undecanoic acid | 1 |
| Phenyl succinic acid | 1 |

Having thus described in detail a preferred embodiment of the present invention, it will be apparent to those skilled in the art that various physical changes could be made in the device described herein without altering the inventive concepts and principles embodied. The present embodiment is therefore to be considered in all respects as illustrative and not restrictive, the scope of the invention being indicated by the appended claims. All changes which come within the meaning and range of equivalency of the claims are therefore to be embraced therein.

We claim:

1. The method of diagnosing diseases which comprises (a) coating the surface of hydrophobic material capable of adsorbing plasma protein with normal blood plasma protein to form a protein-coated surface, (b) measuring the streaming potential characteristic of the protein-coated surface, (c) adding to the protein coating a challenge material capable of altering the electro-kinetic potential of the adsorbed blood plasma protein, thereby forming an altered protein-coated surface, (d) measuring the streaming potential characteristic of the altered protein-coated surface, thereby obtaining control streaming potential values.

(e) repeating procedures (a), (b), (c), and (d) with a patient-blood plasma suspected of being diseased blood plasma, thereby obtaining experimental streaming potential values, and (f) comparing the control and experimental streaming potential values, thereby achieving a diagnosis of the diseased or non-diseased condition of a patient's blood.

2. The method of claim 1 wherein the patient blood plasma comprises the blood plasma of a patient suspected of being afflicted with multiple sclerosis.

3. The method of diagnosing diseases which comprises:

(a) coating the surface of a hydrophobic material capable of adsorbing plasma protein with normal blood plasma protein to form a protein-coated surface, (b) establishing an electric charge on the protein-coated surface, passing an electrolyte solution across the coated surface at a uniform flow rate for measuring a subsequently developed streaming potential, (C) applying to the protein coating a challenge material capable of altering the electro-kinetic potential of the adsorbed blood plasma protein, thereby forming an altered protein-coated surface, (d) establishing an electric charge on the altered protein-coated surface, passing an electrolyte solution across it at a uniform flow rate and measuring a subsequently developed streaming potential, thereby obtaining control streaming potential values, (e) repeating procedures (a), (b), (c), and (d) with a patient blood plasma suspected of being diseased blood plasma, thereby obtaining experimental streaming potential values, and (f) comparing the control and experimental streaming potential values, thereby achieving a diagnosis of the diseased or non-diseased condition of a patient's blood.

4. The method of claim 3 wherein the electrolyte solution has an ionic strength $\mu$ within the range of from about $10^{-1}$ to about $10^{-5}$.

5. The method of claim 3 wherein the electrolyte solution comprises an aqueous sodium chloride solution.

6. The method of claim 3 wherein the electrolyte solution has a pH from about 5 to about 9.

7. The method of claim 3 wherein the electrolyte solution has a pH of from about 6 to about 8.

8. The method of claim 3 wherein the challenge material comprises a fatty acid having from 6 to 24 carbon atoms, inclusive.

9. The method of claim 3 wherein the challenge material comprises a fatty acid having from 16 to 22 carbon atoms, inclusive.

10. The method of claim 3 wherein the challenge material comprises linoleic acid.

11. The method of claim 3 wherein the challenge material comprises oleic acid.

12. The method of claim 3 wherein the challenge material comprises undecenoic acid.

13. The method of claim 3 wherein the surface is coated by adding the blood plasma protein and the challenge material, respectively, to the electrolyte solution, and passing the solution over the plasma protein-adsorbing surface.

14. The method of claim 13 wherein the mixture of plasma and electrolyte solution contains from about 0.1 to about 0.8 grams of plasma per 200 milliliters of electrolyte solution and the mixture has a pH of from about 6 to about 8.

15. The method of claim 3 wherein the disease is multiple sclerosis.

16. The method of claim 15 wherein the plasma is mixed with the electrolyte solution and the surface is coated by passing the solution over the plasma protein-adsorbing surface, the electrolyte solution comprises aqueous sodium chloride having an ionic strength of $\mu$ within the range of from $10^{-1}$ to $10^{-5}$, the pH of the electrolyte solution mixture is from 6 to 8, the electrolyte solution contains from 0.1 grams to 0.8 grams plasma to 200 milliliters of solution, and the challenge material comprises a fatty acid having from 16 to 22 carbon atoms.

* * * * *